(12) United States Patent
Iwamoto et al.

(10) Patent No.: US 9,333,050 B2
(45) Date of Patent: May 10, 2016

(54) GUTTA-PERCHA REMOVER

(75) Inventors: Yukihisa Iwamoto, Tochigi (JP); Norio Kaneko, Tochigi (JP)

(73) Assignee: Mani, Inc. (JP)

( * ) Notice: Subject to any disclaimer, the term of this patent is extended or adjusted under 35 U.S.C. 154(b) by 0 days.

(21) Appl. No.: 13/203,817

(22) PCT Filed: Feb. 25, 2010

(86) PCT No.: PCT/JP2010/052964
§ 371 (c)(1),
(2), (4) Date: Oct. 3, 2011

(87) PCT Pub. No.: WO2010/098385
PCT Pub. Date: Sep. 2, 2010

(65) Prior Publication Data
US 2012/0021376 A1 Jan. 26, 2012

(30) Foreign Application Priority Data

Feb. 27, 2009 (JP) ................................. 2009-045859

(51) Int. Cl.
*A61C 5/02* (2006.01)

(52) U.S. Cl.
CPC .................. *A61C 5/026* (2013.01); *A61C 5/023* (2013.01)

(58) Field of Classification Search
CPC .......... A61C 5/025; A61C 5/023; A61C 5/02; A61C 5/04; A61C 5/026
USPC ..................................... 433/81, 102, 164, 224
See application file for complete search history.

(56) References Cited

U.S. PATENT DOCUMENTS

| | | | |
|---|---|---|---|
| 4,634,378 A | 1/1987 | Leonard | |
| 4,904,185 A | 2/1990 | McSpadden | |
| 5,735,689 A | 4/1998 | McSpadden | |
| 5,762,497 A * | 6/1998 | Heath | 433/102 |
| 6,174,165 B1 | 1/2001 | Katsuumi et al. | |
| 2001/0034005 A1 | 10/2001 | Matsutani et al. | |
| 2002/0119418 A1 | 8/2002 | Matsutani et al. | |
| 2002/0137008 A1* | 9/2002 | McSpadden et al. | 433/102 |
| 2003/0068597 A1 | 4/2003 | Garman | |
| 2005/0282108 A1* | 12/2005 | Goodis | 433/102 |

FOREIGN PATENT DOCUMENTS

| | | |
|---|---|---|
| JP | 59115033 A | 7/1984 |
| JP | 2000083968 A | 3/2000 |
| JP | 2001170076 A | 6/2001 |
| JP | 2001187068 A | 7/2001 |
| JP | 2002253578 A | 9/2002 |
| JP | 3731187 B2 | 1/2006 |

OTHER PUBLICATIONS

International Search Report, directed to International Patent Application No. PCT/JP2010/052964, 4 pages including English translation.

* cited by examiner

*Primary Examiner* — Edward Moran
(74) *Attorney, Agent, or Firm* — Lerner, David, Littenberg, Krumholz & Mentlik, LLP

(57) ABSTRACT

A gutta-percha remover suitable for removing a gutta-percha and having flexibility with good compliancy to curvature of a root canal and a superior removing capability for forming a sufficient gap bet the gutta-percha and the root canal wall is provided. The gutta-percha remover includes a shaft, a tapered working portion connected to the shaft, and one, two, or more screw-shaped grooves formed in the working portion. The cross-sections of a base end and a tip of the working portion are such that the tip of the working portion is greater in rate of the area of each cross-section to a corresponding circle circumscribing the cross-section.

1 Claim, 2 Drawing Sheets

(a)

(b)

GUTTA-PERCHA REMOVER

CROSS-REFERENCE TO RELATED APPLICATION

This patent application is a national phase entry under 35 U.S.C. §371 of International Application No. PCT/JP2010/052964, filed on Feb. 25, 2010, which claims priority to Japanese Patent Application No. 2009-045859, filed on Feb. 27, 2009.

BACKGROUND OF THE INVENTION (1) Field of the Invention

The present invention relates to a dental treatment tool, particularly a gutta-percha remover for removing gutta-percha filled into a root canal.

(2) Description of the Related Art Including Info Disclosed Under 37 CFR 1.97 and 1.98

In dental caries treatment, an operation of cutting a patient's root canal, thereby removing an infected portion, forming it into an appropriate shape, and filling with gutta-percha and a sealer, which is used for filling in a gap between the gutta-percha and root canal wall, as a filler for prevention of subsequent reinfection is performed. Moreover, on the contrary to formation of a root canal, there are also cases where it is necessary to remove the gutta-percha and sealer (referred to as gutta-percha hereafter) filled in the root canal, and an operation of removing the gutta-percha is also performed. As a dental tool for removing the gutta-percha, a reamer or file has been applied since there is no conventional dedicated tool.

However, a problem as described below occurs if a reamer or file is used to remove the gutta-percha. In the case of removing the gutta-percha using a reamer or file, the reamer or file cuts and removes the gutta-percha so as to remove it through a screw-shaped groove of the reamer or file. While only the gutta-percha needs to be removed at this time, since the reamer or file has cutting power, there is fear that the root canal wall is also cut after the gutta-percha is removed, and drawn toward the root apex along with the gutta-percha. If the root canal wall is cut excessively, since a problem such as increase in likelihood of a fracture or perforation of the root canal occurs, it is best to leave healthy tissue as it is if possible.

On the other hand, while the root canal has straight line portions as well as various curved shapes such as spiral shapes, extremely curved shapes at the root apex, and the like according to the individual, there are also problems that the flexure of the reamer or file is not uniform along the length of the working portion and thus cannot follow the shape of the root canal exactly, all of the gutta-percha cannot be removed from the root canal, and the curvature in some instances exceeds the limit, breaking the tip of the tool.

In other words, if the file does not curve uniformly along the length of the working portion, there is an inconvenience that the working portion of the file touches only one side of the curved portion of the root canal and not the other side, some of the gutta-percha remains, and stress concentrates on the tip, thereby fracturing it.

The cross-sectional area of the reamer or file cut orthogonal to a rotational axis of the working portion becomes smaller as it approaches the tip in the same ratio as the tapering ratio of the working portion. With such a structure, it is easy to bend at the tip of the working portion and difficult to bend at the base end of the working portion. Moreover, this is a structure that space (gap between the gutta-percha and the root canal wall) for moving the removed gutta-percha becomes smaller, thereby making it difficult for the gutta-percha to be removed.

In Patent Document 1 (JP Patent No. 3731187), endodontic equipment including tissue removal edges provided unequally spaced on the periphery of a shaft is proposed as an improvement of the above situation. These tissue removal edges can give a more uniform cutting force inside and outside the curvature of the root canal than a conventional symmetrical tool that easily cuts the inside of the curvature of the root canal by a force working on the root canal wall at the curve by the tool.

In Patent Document 2 (JP Patent Publication No. 2002-253578A), a dental reamer having a cross-sectional shape created by cutting along two lines and twisting it such that the center of a circle and two arcs are left is proposed. Such a shape allows improvement in compliance to the curvature of the root canal by increasing flexibility compared to the conventional tool as well as decreasing cutting performance.

In Patent Document 3 (JP Patent Publication No. 2001-170076A), a dental root canal tool including a file with a cross-sectional shape constituted by an arc and a chord is proposed where L is (⅝)D or greater when L is height of the cross section connecting the midpoint of the vertex of the arc and the chord, and D is diameter of the arc. Such a structure allows high flexural rigidity and flexural strength, thereby allowing creation of a path for a reamer or a file ahead of time by penetrating into the root canal.

In Patent Document 4 (JP Patent Publication No. 2000-83968A), the cross-sectional shape of the working portion of the file is oblong. Moreover, an oblong aspect ratio that changes along the length (axial direction) exhibiting different flexibilities is proposed. It utilizes the fact that flexibility increases if the aspect ratio is increased.

PRIOR ART DOCUMENTS

Patent Documents

Patent Document 1: JP Patent No. 3731188
Patent Document 2: JP Patent Publication No. 2002-253578A
Patent Document 3: JP Patent Publication No. 2001-170076A
Patent Document 4: JP Patent Publication No. 2000-83968A However, the tools disclosed in Patent Documents 1 to 3 still have problems that the tip side easily bends and the base end side does not easily bend, and that a cut piece is not easily removed since the cross-sectional area in any of the cases changes at the same rate as the tapering ratio. The tool disclosed in Patent Document 4 has a fear of cutting healthy tissue along with the gutta-percha due to the oblong cross section and superior cutting performance.

BRIEF SUMMARY OF THE INVENTION

The present invention aims to resolve the above-described problem by providing a gutta-percha remover suitable for removing gutta-percha and having flexibility with good compliancy to curvature of a root canal and superior removing capability for forming a sufficient gap between the gutta-percha and the root canal wall.

A gutta-percha remover according to the present invention in order to achieve the above-mentioned aim includes a shaft, a tapered working portion connected to the shaft, and one, two, or more screw-shaped grooves formed in the working portion. As to cross sections of a base end and a tip of the working portion, the tip of the working portion is greater in rate of the area of each cross-section to corresponding circle circumscribing said each cross section.

Configurations in which the cross sections of the working portion is formed by an arc of a circle circumscribing the cross section and a curve connecting both ends of the arc, a rake angle of a rotative tip of the working portion is −50 degrees or less, the area of the cross-section divided by area of the circle circumscribing the cross section is 80±5% at the tip of the working portion and 50±5% at the base end of the working portion, the tip of the working portion is 1.36 time to 1.89 times the base end of the working portion in area of the cross-section divided by area of a circle circumscribing the cross section, thread width along the length of the working portion is almost constant, pitch along the length of the working portion is varied, tapering of the working portion is 2/100 to 10/100, the gutta-percha remover is formed by rounding an edge portion to become a rotative tip of the working portion, rotating speed of the gutta-percha remover connected to a hand piece is 500 to 2000 rpm, and number of threads in the working portion is 6 to 10, are possible.

The gutta-percha remover is attached to a rotational tool, rotation is applied thereto, and the working portion thereof is then pressed against the gutta-percha within the root canal. As a result, in a root canal narrow portion, frictional heat generates in friction due to rotation of the gutta-percha remover and the gutta-percha within the narrow root canal, and the gutta-percha softens so as to stretch and peel off from the root canal. The softened gutta-percha may be caught in a screw-shaped groove that is formed in the working portion of the gutta-percha remover, thereby being removed. While the removed pieces of the gutta-percha are either made up of a unified clump or small strip-cut fragments, these removed pieces may be discharged outside of the root canal through the screw-shaped groove. Since the tip of the working portion is greater in rate of the area of each cross-section to corresponding circle circumscribing said each cross section, the tip and the base end of the working portion are bent uniformly, they may bend in compliance to even various curves of the root canal, and the gutta-percha may be easily removed since the gap between the gutta-percha and the root canal wall on the base end side is large. This allows complete removal of the filled-in gutta-percha without any remaining in the root canal.

Moreover, since the respective cross sections of the working portion are formed by an arc of the circle circumscribing the cross section and a curve connecting both ends of the arc, the rake angle of a rotative tip of the working portion may be set negative, and the areas of the respective cross sections may be adjusted. In particular, the base end side may be made smaller than the tip side of the working portion in rate of the area of the cross-section to that of the circle circumscribing the cross section.

If the rake angle of the rotative tip of the working portion is −50 degrees or less, the gutta-percha may be removed in a unified clump without cutting it since the tool does not have a cutting edge.

DETAILED DESCRIPTION OF THE INVENTION

A gutta-percha remover is externally similar to the aforementioned reamer or file, and thus common points and differences are described below before describing an embodiment of the present invention.

(Common Points)

Common points of the gutter-percha remover and the reamer or file are:

(i) they both have a working portion formed tapered on the tip side with equal length and width;

(ii) one or two or more screw-shaped grooves are formed in the working portion; and (iii) they both have flexibility allowing bending along curvature of the root canal.

(Differences)

Meanwhile, the differences of the gutter-percha remover and the reamer or file are:

(i) while the reamer or file has a cutting blade for cutting the root canal wall, the gutter-percha remover does not have a cutting blade for cutting the root canal wall;

(ii) while the reamer or file is mainly used by rotating it by hand or moving it axially, the gutter-percha remover is used as a rule by attaching it to a rotational tool such as a hand piece and rotating it electrically;

(iii) while the reamer or file has a working portion with a tapering of approximately 2/100, the gutter-percha remover has a working portion with a greater tapering of up to approximately 10/100;

(iv) while multiple sets of the reamer or file slightly increasing in size are used to perform root canal formation, two to three of the gutter-percha removers selected according to degree of root canal curvature of the root canal and size of root canal aperture are used to remove gutter-percha;

(v) while the reamer or file has a tip diameter of approximately 0.06 to 1.4 mm since its objective is root canal formation, the gutter-percha remover has a tip diameter (since it is a tool for removing gutter-percha from an already formed root canal) of approximately 0.2 to 1.0 mm;

(vi) while the working portion of the reamer or file has a length of 16 mm, the working portion of the gutter-percha remover has a length of approximately 12 mm to 16 mm; and (vii) when tools with a tip diameter between 0.3 to 0.7 mm are compared, the reamer or file has 9 to 28 threads, and the gutter-percha remover has 6 to 10 threads.

Next, the embodiment of the present invention is described while referencing the attached drawings.

Figure 1:
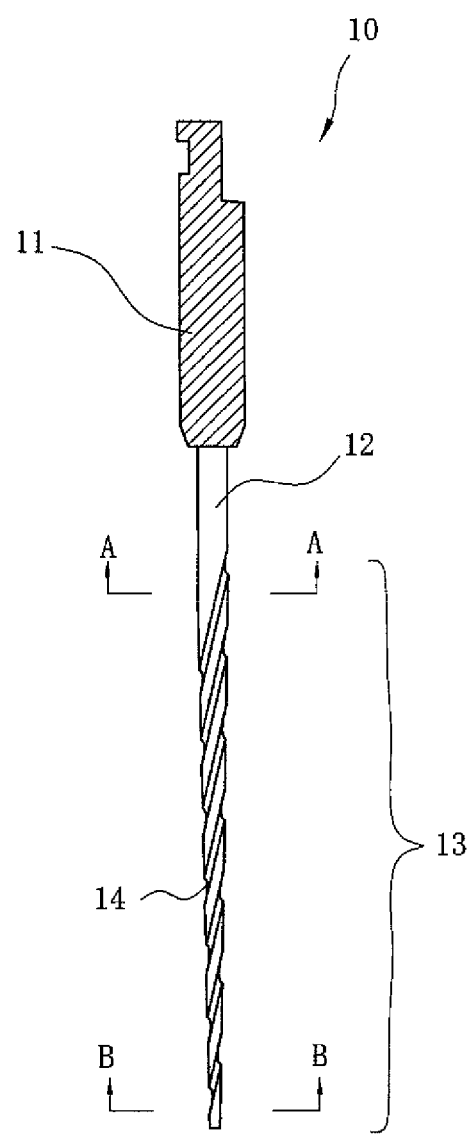
FIG. 1 is a front view of a gutta-percha remover according to the present invention.

FIG. 1 is a front view of a gutta-percha remover according to the present invention. A gutta-percha remover 10 has on one end a gripper 11 to be attached to a rotational tool, to which a shaft 12 is connected. A tapered working portion 13 is formed on the shaft 12. Stainless steel or a Ni—Ti material is used for a portion ranging from the shaft 12 to the working portion 13. More specifically, the Ni—Ti material is a shape-memory alloy and has superior flexibility as it is a superelastic body. Moreover, in the case of stainless steel, use of a material resulting from wire-drawing austenitic stainless steel to form a fibrous crystalline structure is desired.

The working portion 13 is tapered. The reamer or file is also tapered, where in that case, the tapering is approximately 2/100. On the other hand, while the root canal is also tapered, this tapering is approximately 5/100 to 7/100, which is greater than that of the reamer or file. While the gutta-percha remover 10 needs to have tapering within the range of 2/100 to 10/100, various sorts of tapering are available depending on the root canal region used. In the case of a straight portion at the entrance of the root canal, tapering of approximately 4/100 to 10/100 is preferable, and in the case of a curved portion deep in the root canal, tapering of approximately 3/100 to 5/100 is preferable. By employing such tapering, running torque easily reaches the gutter-percha, and removal of the gutter-percha is easily performed. Note that while it is omitted from the drawing, tapering may be gradually increased from the tip toward the base end without giving it a uniform taper. For example, tapering at the tip may be set to 2/100 and gradually changed so as to be 7/100 at the base end.

A screw-shaped groove 14 is formed in the working portion 13. This screw-shaped groove 14 is formed by grinding using a grindstone. While it is difficult to form a screw-shaped groove by twisting in the case of a Ni—Ti material, the screw-shaped groove 14 may be easily formed by grinding. Moreover, while several screw-shaped grooves are formed if the screw-shaped groove 14 is formed by twisting, formation of only one groove is possible by grinding.

With the gutta-percha remover 10 of the present invention, in order that gutter-percha is not pulled toward the root apex but is easily removed as a combined clump, pitch of the screw-shaped groove 14 in the illustrated embodiment is greater than that of the reamer or file. Moreover, the pitch may be made constant or changed throughout the entire working portion 13. However, if the pitch of the screw-shaped groove 14 is made smaller on the tip side and larger on the base end side, fatigue fracture characteristics improve and a fracture is more unlikely to occur.

Furthermore, while the pitch consists of thread width and groove width, bending along the length of the working portion may be made uniform by setting the thread width approximately constant. For example, with the tool 10 where the tip diameter is 0.3 mm and length of the working portion is 16 mm (used at a curved region of the root canal), the thread width is formed constant at 0.9 mm from the tip to the base end of the working portion, pitch at the very tip is set to 1.3 mm (0.4 mm groove width), pitch at the very base end is set to 1.8 mm (0.9 mm groove width), and number of threads is set to ten. Alternatively, with the tool 10 where the tip diameter is 0.7 mm and length of the working portion is 12 mm (used at a straight region of the root canal), the thread width is set to 0.9 mm at the very tip and 1 mm at the very base end of the working portion, pitches are set to 1.65 mm (0.75 mm groove width) and 1.8 mm (1.2 mm groove width), respectively, and number of threads is set to 6. It is preferable that the thread width is approximately constant in this manner, and formation by changing it across approximately 0 to 25% of the entire length of the working portion while keeping balance with the groove depth allows uniform bending along the entire length of the working portion.

While the tip of the tool 10 is formed as a flat surface in FIG. 1, it may be formed in a hemispherical shape or the like and structured so as to heighten safety (difficulty to cut) during use at high-speed rotation.

Figure 2:
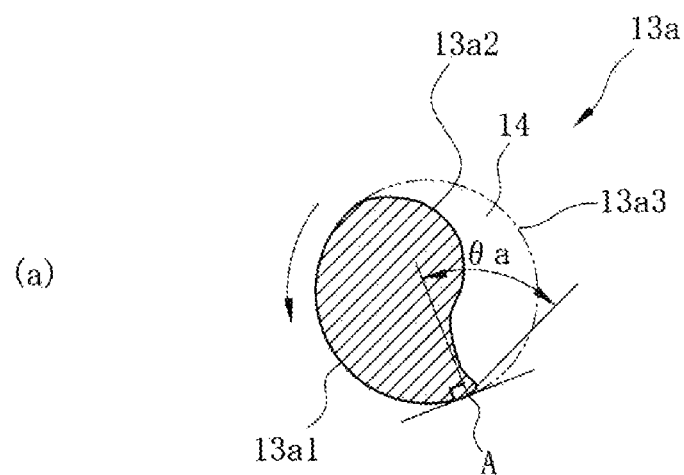
FIG. 2A shows a cross-section view of a working portion cut along the line A-A of FIG. 1.
FIG. 2B is a cross-sectional view cut along the line B-B of FIG. 1
Figure 2:
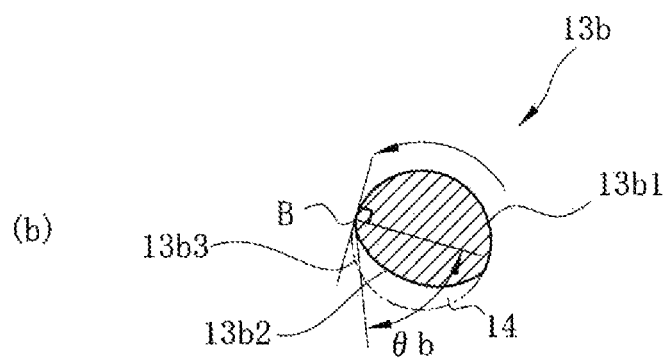

FIG. 2A shows a cross-sectional view cut along the line A-A of FIG. 1, and FIG. 2B is a cross-sectional view cut along the line B-B of FIG. 1. The A-A cross-sectional view is a cross section of the base end (a portion approximately 16 mm from the tip) of the working portion, and B-B cross-sectional view is a cross section of the tip (a portion approximately 3 mm from the tip) of the working portion.

A cross section 13a of the base end of the working portion 13 shown in FIG. 2A is formed from an arc 13a1 having a length of 40% or more of a circumscribed circle, and a curve 13a2 connecting both ends of the arc 13a1. The arc 13a1 is a part of a circumscribed circle 13a3 of the cross section 13a. It is configured such that the curve 13a2 is wavy, both ends of the cross section 13a are connected by a convex curve (formed according to a certain radius not forming a cutting blade) on the outside of the circumscribed circle so as not to have a cutting function, and the central portion has a small cross-sectional area made up of the center of the circle and a concave curve (convex on the inside of the circumscribed circle). Area of the cross section 13a is 50±5% of area of the circumscribed circle 13a3.

A cross section 13b of the tip of the working portion 13 shown in FIG. 2B is formed from an arc 13b1 having a length of 50% or more or a circumscribed circle, and a curve 13b2 connecting both ends of the arc 13b1 in a convex shape. The arc 13b1 is a part of a circumscribed circle 13b3 of the cross section 13b. Area of the cross section 13b is 80±5% of area of the circumscribed circle 13b3. The area of the cross section 13b of the base end of this working portion is accordingly 1.36 to 1.89 times that of the cross section 13a of the tip of the working portion. In this manner, by a configuration such that depth of the screw-shaped groove 14 is deep on the base end side of the working portion, gradually becoming shallow toward the tip side, it is possible to facilitate penetration to the gutta-percha so as to convey a running torque, as well as removal of the gutta-percha.

The gutta-percha remover 10 is rotated in the arrow direction FIG. 2A or 2B, thereby grinding the root canal wall at point A and point B, respectively, which become the rotative tip. While point A and point B respectively become a cutting blade tip in the case of a reamer or file, the gutta-percha remover 10 of the present invention does not have a function as a cutting blade, where both a rake angle θb at point B are −50 degrees or less, which is further negative than that with the reamer or file. In addition to negative rake angles, rounded point A and point B may be formed. In other words, the gutta-percha remover 10 of the present invention does not have a cutting blade. Therefore, while the gutta-percha may be caught in a screw-shaped groove and then removed, the root canal wall made of healthy dentin cannot be removed.

Next, how to use the gutta-percha remover 10 of the present invention is described.

First, two gutta-percha removers are prepared. The first one should be made of stainless steel and have excellent flexural strength and penetrating ability. Since this tool applies running torque and frictional pressure to hardened gutta-percha at the aperture of a root canal, flexibility is not often required. This first remover is attached to a rotational tool, 500 to 2000 rpm rotation is applied thereto, and it is then pressed against the aperture of the root canal. If the tip of the gutta-percha remover 10 given strength by increasing its cross-sectional area touches the gutta-percha and rotates, thereby generating frictional heat, the gutta-percha becomes a softened, combined clump. The combined clump is caught in the screw-shaped groove 14 of the remover 10 and then removed. Alternatively, the gutta-percha caught in the screw-shaped groove 14 is cut into strips through rotation. The strip-cut fragments are then removed through the screw-shaped groove 14. The gutta-percha until just before the root canal curves is removed in this manner.

Next, a gutta-percha remover 10 made of Ni—Ti alloy with excellent flexibility is attached as the second gutta-percha remover to a rotational tool. 500 to 2000 rpm rotation is applied thereto, and it is then pressed against the portion of the root canal beginning to curve. The tip of the gutta-percha remover 10 digs into the gutta-percha and moves through it while curving along the curve of the root canal. If frictional heat is generated due to rotational friction, the gutta-percha becomes a softened, combined clump. The combined clump is caught in the screw-shaped groove 14 of the remover 10 and then removed. Alternatively, the gutta-percha caught in the screw-shaped groove 14 is cut into strips through rotation. The strip-cut fragments are removed through the screw-shaped groove 14, thereby removing the gutta-percha from the root canal. While the root canal wall is exposed at the portion where the gutta-percha is gone, there is no reason to cut since the remover 10 does not have a cutting blade. Moreover, the sealer used when filling in the gutta-percha is mostly pealed off from the root canal wall along with the gutta-percha and removed to the outside.

DESCRIPTION OF REFERENCE NUMERALS

10: gutta-percha remover
11: gripper
12: shaft
13: working portion
13a: cross section of base end
13a1: arc
13a2: curve
13a3: circumscribed circle
13b: cross section of tip
13b1: arc
13b2: curve
13b3: circumscribed circle
14: screw-shaped groove
θa: rake angle
θb: rake angle

The invention claimed is:
1. A gutta-percha remover comprising:
a gripper to be attached to a rotational tool;
a shaft connected to the gripper;
a tapered working portion connected to the shaft; and
one, two, or more screw-shaped grooves formed in the working portion,
wherein the working portion comprises a base end and a tip, with the one, two, or more screw-shaped grooves having a gradually reducing depth from the base end toward the tip of the working portion,
wherein tapering of the working portion is from 3/100 to 10/100,
wherein an area of a cross-section of the tip divided by an area of a circle circumscribing the cross-section of the tip is greater than an area of a cross-section of the base end divided by an area of a circle circumscribing the cross-section of the base end,
wherein the circumference of the cross-section of the tip of the working portion is formed from an arc having a length of 50% or more of the circle circumscribing the cross-section of the tip and a convex curve connecting a first end of the arc and a second end of the arc in a convex shape, wherein said convex shape extends from the first end of the arc to the second end of the arc, and the circumference of the cross-section of the base end of the working portion is formed from an arc having a length of at least 40% of the circle circumscribing the cross-section of the base end and a curve connecting both ends of the arc of the cross-section of the base in a substantially S-shaped wave that has a convex portion and a concave portion,
wherein the working portion has a negative rake angle, and points where the arc and the curve of the base end meet on the circle circumscribing the cross-section of the base end, and points where the arc and the curve of the tip meet on the circle circumscribing the cross-section of the tip, are rounded,
wherein the gutta-percha remover lacks a cutting blade and does not function as a cutting blade.

* * * * *